United States Patent [19]

Ueki

[11] Patent Number: 5,366,492
[45] Date of Patent: Nov. 22, 1994

[54] DISPOSABLE BODY WARMER
[75] Inventor: Akio Ueki, Osaka, Japan
[73] Assignee: Kiribai Chemical Industry Co., Ltd., Osaka, Japan
[21] Appl. No.: 109,060
[22] Filed: Aug. 19, 1993
[51] Int. Cl.⁵ .............................................. A61F 7/00
[52] U.S. Cl. ................................... 607/114; 126/263; 252/67
[58] Field of Search ...................... 607/96, 108–112, 607/114; 126/263; 252/67

[56] References Cited

U.S. PATENT DOCUMENTS

| | | |
|---|---|---|
| 32,026 | 11/1985 | Yamashita . |
| 3,951,127 | 4/1976 | Watson et al. . |
| 4,114,591 | 9/1978 | Nakagawa ...................... 607/114 X |
| 4,268,272 | 5/1981 | Taura . |
| 4,282,005 | 8/1981 | Sato et al. . |
| 4,649,895 | 3/1987 | Yasuki et al. . |
| 4,756,299 | 7/1988 | Podella ........................... 607/114 X |
| 5,046,479 | 9/1991 | Usui ................................ 607/114 X |

Primary Examiner—Angela D. Sykes
Attorney, Agent, or Firm—Armstrong, Westerman, Hattori, McLeland & Naughton

[57] ABSTRACT

A disposable body warmer comprising a flat inner bag, heat-generating component which generates heat under presence of air being enclosed in the flat inner bag and an airtight bag enclosing the flat inner bag therein, characterized in that the heat-generating component contains potassium chloride, water, water-holding material, activated carbon and iron powder. With the disposable body warmer of the present invention, time required to reach a predetermined temperature from just after beginning of exothermic reaction is short, and duration in the predetermined temperature is long.

14 Claims, 6 Drawing Sheets

DISPOSABLE BODY WARMER

BACKGROUND OF THE INVENTION

The present invention relates to a disposable body warmer, and more particularly to a disposable body warmer which has a good rising (i.e. the rising in temperature is fast) and can maintain a predetermined high temperature condition for a long time.

A disposable body warmer is based on the fact if air is supplied to a mixture comprising metal powder available with relatively low cost such as iron powder and assistance such as water, wood flour and sodium chloride contained in an air-permeable bag, it generates heat. The disposable body warmer is easy to carry and can be easily used by merely openning an outer bag, so that it occupies a major proportion of body warmers in these days.

In such disposable body warmers, sodium chloride has generally been used as a catalyst to promote exothermic reaction. However, the body warmer with sodium chloride as a catalyst does not always bring satisfaction with regard to rising rate in temperature, duration and warmness, because sodium chloride is unevenly oxidized.

In view of the above-mentioned circumstance, it is an object of the present invention to provide a disposable body warmer with which the conventional problem is solved. That is, it is an object of the present invention to provide a disposable body warmer with which time required to reach a predetermined temperature from just after beginning of exothermic reaction is short, and duration at the predetermined temperature is long.

SUMMARY OF THE INVENTION

In a disposable body warmer of the present invention, heat-generating component is enclosed in a flat bag, the component being oxidized and generating heat under presence of air, and this flat bag is enclosed in an airtight bag. The disposable body warmer is characterized in that the heat-generating component contains potassium chloride, water, water-holding material, activated carbon and iron powder.

Proportion of potassium chloride is preferably 0.5% to 10% (% by weight, hereinafter the same), and more preferably 1.5% to 5.0%. Proportion of water is preferably 10% to 35%, and more preferably 25% to 30%.

Preferably the heat-generating component further contains at least one member selected from the group consisting of iron sulfide, soda thiosulfate and potassium thiosulfate.

Further, one surface of the flat bag is preferably provided with self-adhesive layer wholly or partially. This adhesive layer is preferably formed in a stripe.

DETAILED DESCRIPTION

A disposable body warmer of the present invention is explained in detail hereinafter.

Figure 1:
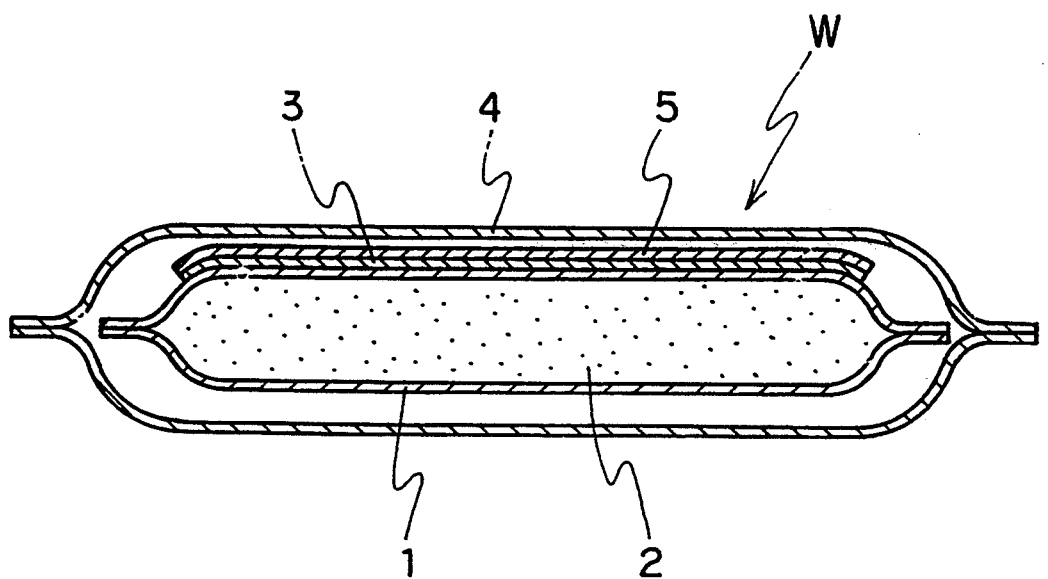
FIG. 1 is a sectional explanatory view of an embodiment of a disposable body warmer of the present invention.
Figure 2:
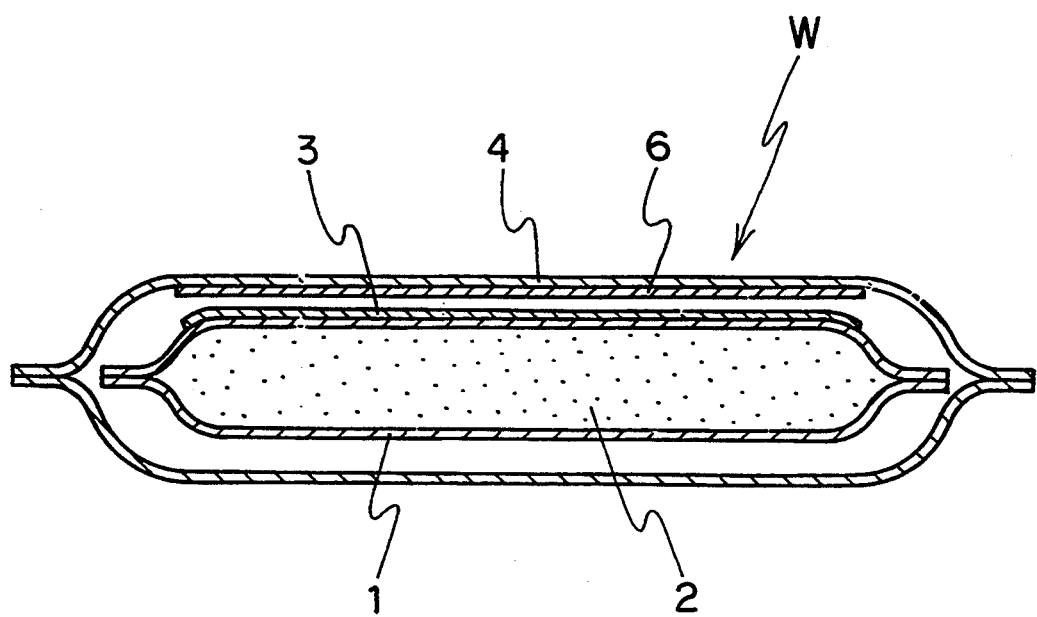
FIG. 2 is a sectional explanatory view of another embodiment of a disposable body warmer of the present invention.

In FIGS. 1 to 2, symbol W represents a disposable body warmer of an embodiment of the present invention. The body warmer W is composed of a flat inner bag 1, heat-generating component 2 contained in the inner bag 1, a self-adhesive layer 3 formed on one surface of the inner bag 1, and an airtight outer bag 4 containing the inner bag 1.

One surface of the flat bag 1 is air permeable while the other surface thereof is air impermeable. In the embodiment shown in FIGS. 1 to 2, the under surface of the inner bag 1 is made air permeable. In producing the inner bag 1, both surfaces thereof might be made of air permeable material and one surface might be made air impermeable or air adjustable by applying a self-adhesive layer 3 entirely or partially on one surface. There might also be employed an inner bag in which one surface thereof is firstly made air permeable while the other surface thereof is made air impermeable and a self-adhesive layer is applied on the air impermeable surface entirely or partially. In short, at least one surface of the inner bag is air permeable, and a self-adhesive layer is formed on either surface entirely or partially.

With respect to air permeability of the inner bag 1, it is possible to select material for the inner bag 1 based on "air permeability" (sec/100 ml: time (sec) required for a given amount of air (100 ml) to pass through an unit area (645 mm$^2$) under pressure, and in airtight bag enclosed in the flat inner bag P 8117). Evaluation based on the "air permeability", however, has drawbacks that there is a large scatter in results due to features of test method employing forced air passage, resulting in an inferior accuracy, and it requires expensive analysis cost and a long test time. Accordingly, for selecting material for the inner bag, instead of the "air permeability", there is preferably employed "water vapor permeability" (g/m$^2$·24h: An amount of water vapor passing through a film of an unit area in a given period of time. According to condition B in JIS Z 0208, a vaporproof package material is used as a boundary surface. The relative humidity of air on one side is kept 90% while air on the other side is kept dry by moisture-absorbing agent at 40° C. The mass (g) of water vapor passing through the boundary surface within 24 hours is converted into a value per 1 m$^2$ of the surface.). Preferable "water vapor permeability" is 340 to 1000 g/m$^2$·14h, and more preferably 350 to 700 g/m$^2$·24h. Though the other factors influence, in general, if "water vapor permeability" is less than 340 g/m$^2$·24h, there are disadvantages that sufficient exothermic reaction cannot be obtained, i.e. the temperature of body warmers is not raised. On the other hand, if "water vapor permeability" is more than 1000 g/m$^2$·24h, there are disadvantages that body warmers become too hot, duration is short, and body warmers inflate during or after use.

Though materials for the inner bag 1 are not limited in the present invention, it is preferable to use such materials that have good fitness to the human body, underwears and the like, stable quality, applicability for heat sealing, and are soft and strong, not nappy. Usable concrete examples are, for example, plastic-like or rubber-like flexible thermoplastic sheet or film comprising polyurethane, polypropylene or polyethylene, or modifications thereof; and a single layer or complex layer of non-woven fabric, polyvinyl chloride, polyester or polystyrene. As a method for controlling air permeability of an air permeable surface of an inner bag 1, there is a method wherein appropriate heat welding treatment is applied to a sheet or film on which minute continuous pores are formed. Concretely speaking, the air permeability can be controlled, for example, by uniformly distributing or entirely applying heat welding agent which is heated appropriately on a sheet or film having uniform continuous pores of 1 to 50 μm in diameter.

The air permeability can be also controlled by laminating a resin film, on which minute air permeable pores are formed, to a non-woven fabric.

It is preferable that the sheet or film is coloured so that sealed condition can be monitored from colour change at sealing.

Though the size of the inner bag 1 is not particularly limited in present the invention, inner bags of a size from 4×6 cm to 15×20 cm can be usually employed.

Numeral 2 represents a heat-generating component, which is oxidized and generates heat under presence of air, comprising potassium chloride, water, water-holding material (wood flour, vermiculite, diatomaceous earth, pearlite, silica gel, alumina, water-absorbing resin and the like), iron powder and activated carbon. In this specification, the term "heat-generating component" means all compositions contained in the body warmer. With respect to iron powder, water-holding material and the like, those which are used in the usual disposable body warmers can be used.

The present invention is characterized by the fact that as a promoting agent for heat-generating at oxidation reaction of iron powder, potassium chloride is employed whereas sodium chloride was conventionally used. Thanks to the superior promoting function for heat-generating of potassium chloride, the time required for temperature rising is made short and its duration is made long than in the case of sodium chloride. Though the proportion of potassium chloride is not particularly limited in the present invention, it is usually 0.5% to 10% and preferably 1.5% to 5.0%. If the proportion is less than 0.5% the heat-generating reaction would be spoiled, and if the proportion is more than 10%, oversaturated potassium chloride would be produced to badly influence the productivity of disposable body warmers.

As the activated carbon, usual ones can be employed. However, it is preferable that high performance activated carbon having specific properties described below is employed. That is, in the disposable body warmer of the present invention, high performance activated carbon having an "iodine adsorption power" of 800 to 1200 mg/g and a "methylene blue decoloring power" of 100 to 300 mg/g is preferably used. The "iodine adsorption power" is determined, as prescribed in JIS K 1474, as follows. That is, iodine solution is added to samples and a supernatant liquid is separated after adsorption. Then, a starch solution as an indicator is added thereto to titrate with a sodium thiosulfate solution. The "iodine adsorption power" is determined from the concentration of the remaining iodine. The "methylene blue decoloring power" is determined, as prescribed in JIS K 1470, as follows. That is, methylene blue solution A is added to samples and filtration is carried out after shaking by a shaker. The chromaticity of the filtrate is compared with that of methylene blue solution B, and the "methylene blue decoloring power" is determined from the amount of added methylene blue solution A required for making the chromaticity of filtrate the coincide with that of methylene blue solution B. Both the factors relate to adsorption performance of activated carbon. By using activated carbon having a specific range of adsorption performance, it becomes possible to shorten the time required for raising temperature of disposable body warmers up to a predetermined temperature just from the beginning of heat generation, and to lengthen duration.

Further, it is preferable to add 2 to 6% of silica gel and/or alumina to the above-mentioned heat-generating component 2, so that bulging of the inner bag and agglomeration of the heat-generating component after the beginning of use can be effectively prevented.

If the proportion of silica gel and/or alumina is less than 2%, the inner bag bulges or the heat-generating component agglomerates after the beginning of use. On the other hand, if the proportion is more than 6%, the amounts of other components such as iron powder, water-holding material, activated carbon, potassium chloride and the like are not ideal, so that the body warmer becomes bulky and effects of the other components are lessened. That is, the time required for raising temperature of the heat-generating component up to a predetermined temperature just after the beginning of heat generation is lengthened or duration is shortened.

Further, it is preferable that the heat-generating component contains at least one member selected from the group consisting of iron sulfide, sodium thiosulfate and potassium thiosulfate in order to prevent the bulging of the inner bag. Though the proportion thereof is not particularly limited, it is usually about 0.1% to 1.0%.

As to proportion of water, it is generally about 25% to 30% in conventional body warmers. However, in the present invention, the proportion of water is preferably set in about 10% to 35%. This provides various body warmers with different durations.

Numeral 3 represents a self-adhesive layer comprising usual self-adhesive materials including rubber and the like as a main material. The self-adhesive layer 3 is provided on one surface of the inner bag 1. The self-adhesive layer 3 might be provided entirely on one surface of the inner bag 1, or might be provided partially so as to form suitable patterns such as a stripe pattern, a grid pattern and polka dots. The self-adhesive layer 3 is formed after the above-mentioned heat-generating component 2 is charged into the inner bag 1.

In the embodiment shown in FIG. 1, a release paper 5 covers the surface of the self-adhesive layer 3. In use, the release paper 5 is released off, and the inner bag 1 is adhered to a desired portion utilizing the self-adhesive layer 3.

Numeral 4 represents an airtight outer bag comprising a poreless film made of polyethylene, polypropylene and the like. In the embodiment shown in FIG. 2, the release layer 6 is formed on the inner surface of the outer bag, whereby covering and protecting the self-adhesive layer 3 formed on the inner bag. In this case, the outer bag 4 functions also as a release paper in the conventional body warmer, so that the inner bag 1 can be fixed to a desired portion by merely opening the outer bag 4.

As a self-adhesive layer, various embodiments can be employed other than above mentioned. These embodiments will be described below with reference to the drawings.

Figure 3:
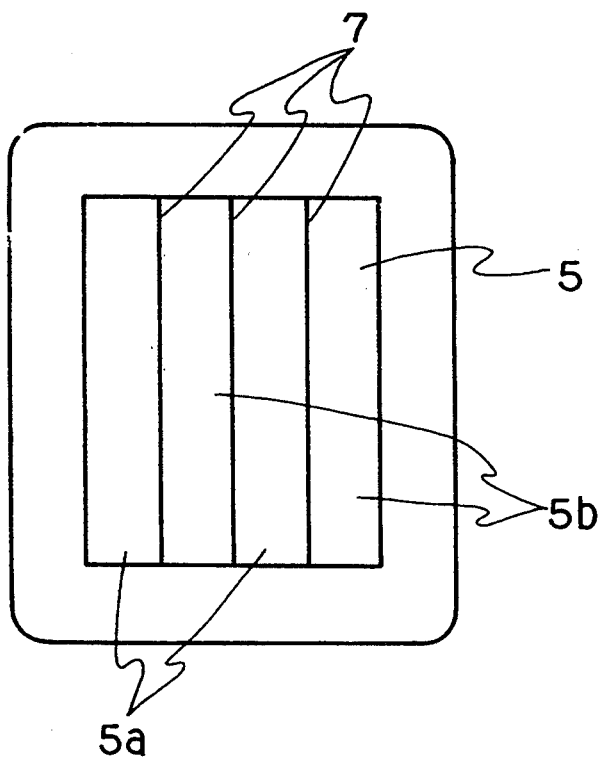
FIG. 3 is an explanatory plan view of an inner bag in a further embodiment of a disposable body warmer of the present invention.

In an embodiment shown in FIG. 3, three slits 7 are formed in parallel with each other to release paper 5. In use, one releases the release paper 5a and attaches the body warmer to a desired position. Thereafter, if wishing to again attach the warmer to other position, one releases the release paper 5b, so that the warmer can surely be attached. The number of slits 7 is not limited in the present invention. At least one slit is enough and the formed position thereof can be selected freely.

Figure 4:
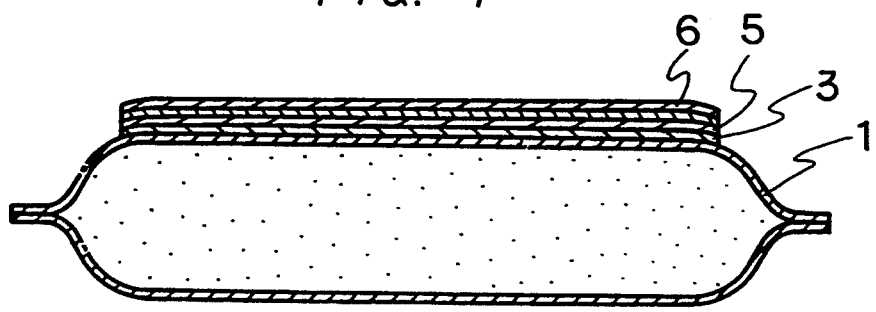
FIG. 4 is a sectional explanatory view of an inner bag in a further embodiment of a disposable body warmer of the present invention.

In an alternative embodiment shown in FIG. 4, a plurality of self-adhesive layers are formed so as to permit the body warmer to be attached twice or more. Numeral 3 represents a self-adhesive layer formed on one side of the inner bag 1. Numeral 5 represents a release paper on which one side a self-adhesive layer is formed. This release paper 5 is provided on the self-adhesive layer 3 of the inner bag I with the self-adhesive layer of the release paper 5 facing outward (opposite side to the flat bag). Numeral 6 represents a release paper. This embodiment is designed so that the release papers are released in sequence to make another self-adhesive layer appear, thereby permitting the body warmer to be attached plural times. In the embodiment shown in FIG. 4, the number of the release paper which has a self-adhesive layer on one side thereof is one, but two or more release papers of such a type might be employed.

Figure 5:
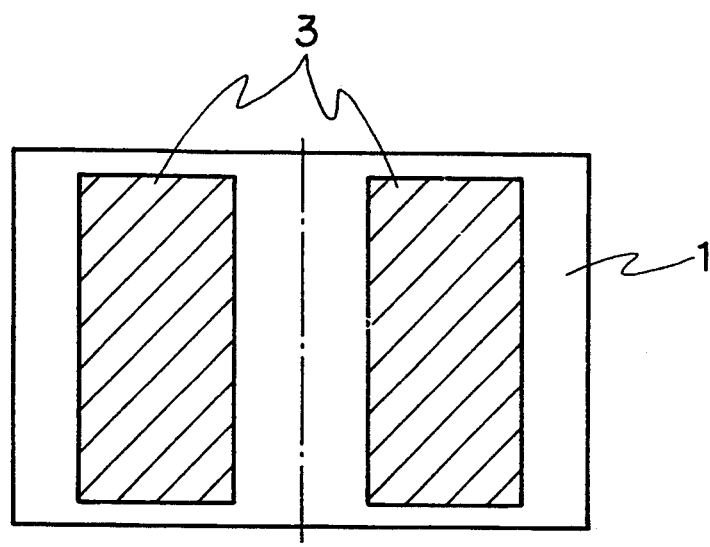
FIGS. 5 and 6 are explanatory plan view of an inner bag in a further embodiment of the present invention.

FIG. 5 shows a further alternative embodiment wherein two self-adhesive layers are formed on one side of the inner bag. The inner bag 1 is folded so that the two self-adhesive layers 3 thereof are detachably stuck to each other. FIG. 5 shows an unfolded state of the embodiment for ease of understanding.

Figure 6:
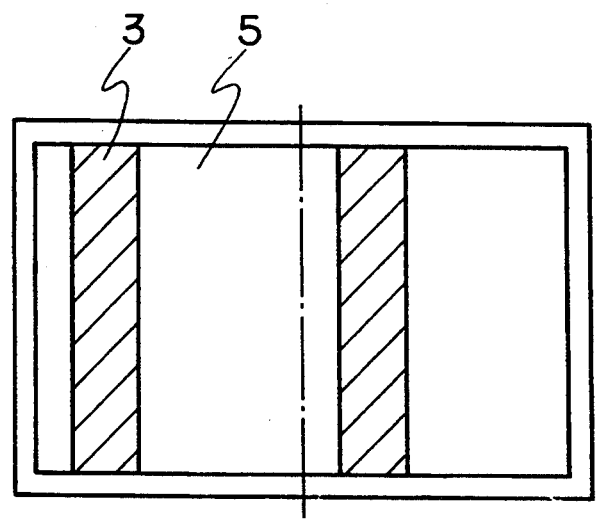

In an embodiment shown in FIG. 6, a release layer 5 is formed in such a position as to cover a self-adhesive layer 3 when the body warmer assumes a folded position.

Figure 7:
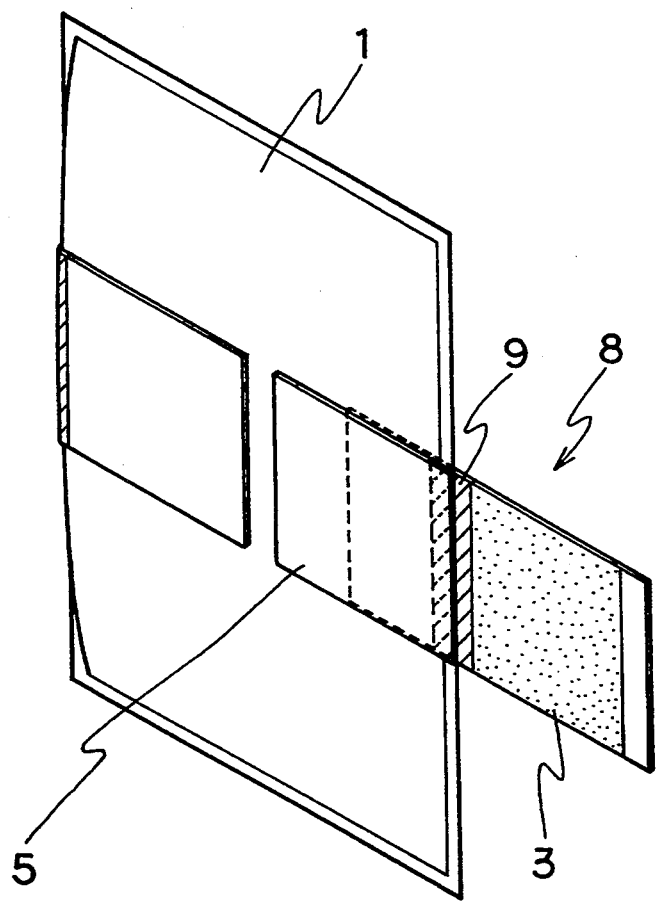
FIGS. 7 and 8 are explanatory view of an inner bag in further embodiment of the present invention.

In an embodiment shown in FIG. 7, a self-adhesive tongue piece 8 is provided on the inner bag 1. This tongue piece 8 is provided at one side thereof with a self-adhesive layer 3 and at one end thereof a retractable tape 9. The self-adhesive layer 3 of the tongue piece 8 is stuck on a release layer 5 formed on one side of the inner bag 1, while the end portion adjacent the tape 9 is secured to the inner bag at an opposite side to the side where the release layer is formed. In use, the self-adhesive tongue piece 8 is released from the release layer 5 to be attached to a desired portion while appropriately adjusting the location for the attachment with the retractable tape 9.

Figure 8:
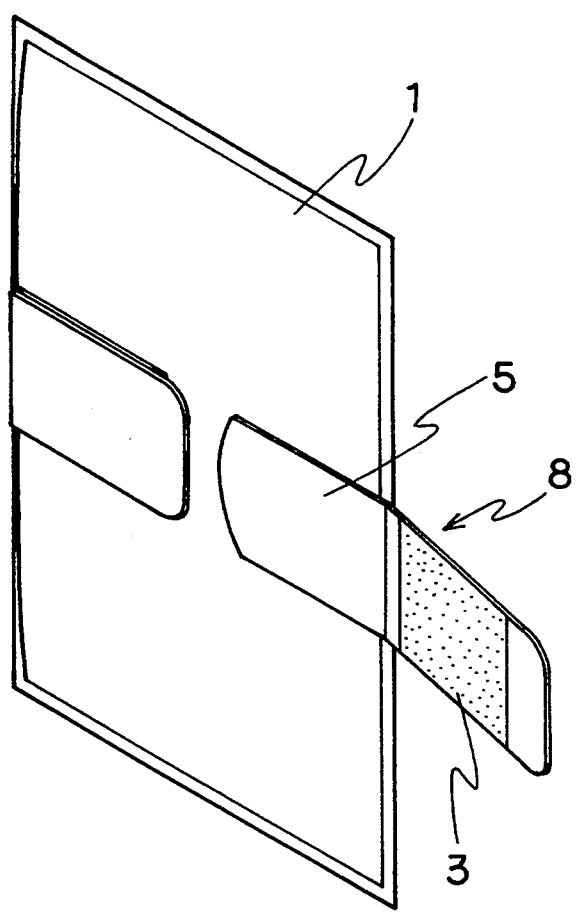

In an embodiment shown in FIG. 8, a self-adhesive tongue piece 8 is used in which a self-adhesive layer 3 is formed on one side thereof so as to be stuck to a release layer 5 when the tongue piece 8 assumes its folded position. This self-adhesive tongue piece 8 is secured to the inner bag 1 at an opposite face to the :face where the release layer 5 is formed.

Instead of the self-adhesive layer, there can be used a slip-stop layer composed of a synthetic resin foam sheet or the like, which is of a foam structure having an air-permeable property at its surface, for example, of a structure wherein at least one side surface of the sheet forms a flat, continuous resin face having fine pores which are contiguous to inner pores having a larger diameter than the fine pores, the inner pores being contiguous among others through fine tubular pores.

The disposable body warmer of the present invention is explained below based on Examples. The present invention is not, however, limited thereto.

The experiments were carried out with random proportion of heat-generating component (refer to Table 1), with maintaining "water vaper permeability" constant (500 g/m$^2$·24h). Measurement was performed on the basis of JIS S 4100, and maximum temperature (° C.), rise-time (minute), duration (hour) and generated amount of gas (ml) were examined.

The number of samples tested was 10, and maximum temperature, rise-time, duration and generated amount of gas were obtained as follows.

MAXIMUM TEMPERATURE

Figure 9:
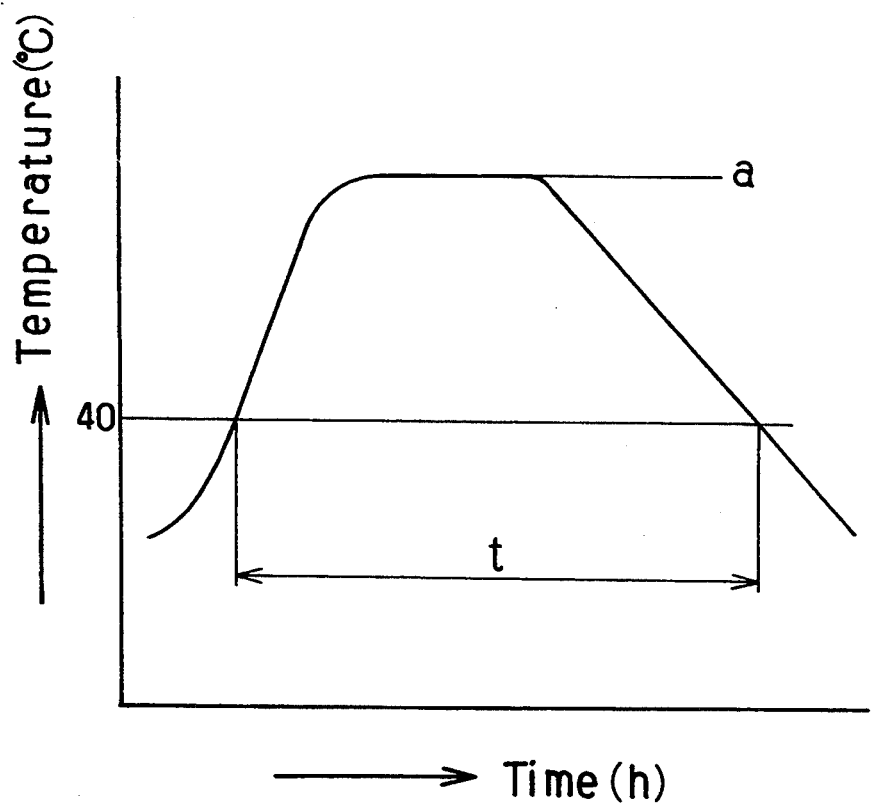
FIG. 9 is a view showing a pattern of temperature change of a disposable body warmer.

Average of measured maximum temperatures of all samples. Refer to a in FIG. 9.

RISE-TIME

Average of measured times of eight samples required for raising temperature up to 40° C. from the beginning of heat generation, wherein the maximum value and minimum value are excluded (provided that only one value of plural miximum values or minimum values is excluded when there are plural maximum values or minimum values).

DURATION

Average of measured durations of eight samples from the beginning of heat generation to the passage of maximum temperature, wherein the maximum value and minimum value are excluded (provided that only one value of plural maximum values or minimum values is excluded when there are plural maximum values or minimum values, and that a fraction less than one hour is omitted). Refer to t in FIG. 9.

GENERATED AMOUNT OF GAS 36 g of heat-generating component is enclosed in an inner bag and sealed therein. This inner bag is evacuatedly enclosed in an outer bag. Initial volume of the outer bag is measured. This outer bag is kept in a thermostatic chamber for 20 hours at 70° C. After sufficiently cooling the outer bag, its volume is measured again and the difference to the initial volume calculated. This calculated difference is defined as generated amount of gas.

EXAMPLE 1

There were prepared inner bags (length: 130 mm, width: 95 mm, sealed width: 6 mm) wherein a lamination of porous polyethylene and nylon non woven fabric which was heat welded to control air permeability was used as art air permeable surface, and polyethylene having thereon an acrylic self-adhesive layer was used as an air impermeable surface. In these inner bags, 36 g of heat-generating component proportioned as shown in Table 1 is filled. The heat-generation performance and the generated amount of gas of thus prepared heat-generator is measured as described above. The result thereof is shown in Table 2.

TABLE 1

| | Heat-Generating Component (%) | | | | | | | | |
|---|---|---|---|---|---|---|---|---|---|
| | Potassium Chloride | Sodium Chloride | Water | Sodium thiosulfate | Water-Holding Material | | | Activated Carbon | Iron Powder |
| | | | | | Vermiculite | KI Gel | Silica Gel | | |
| Ex. 1 | 1.51 | — | 27.52 | 0.13 | 3.41 | 1.92 | 2.04 | 7.91 | 55.56 |
| Ex. 2 | 4.5 | — | 22.0 | — | 7.1 | 1.9 | — | 3.5 | 61.0 |
| Ex. 3 | 4.5 | — | 18.0 | — | 8.7 | 2.3 | — | 4.0 | 62.5 |
| Com. Ex. 1 | — | 1.51 | 27.52 | 0.13 | 3.41 | 1.92 | 2.04 | 7.91 | 55.56 |
| Com. Ex. 2 | — | 4.5 | 22.0 | — | 7.1 | 1.9 | — | 3.5 | 61.0 |
| Com. Ex. 3 | — | 4.5 | 18.0 | — | 8.7 | 2.3 | — | 4.0 | 62.5 |

TABLE 2

| No. | Maximum Temperature (°C.) | Rise-time (minute) | Duration (hour) | Generated Amount of Gas (ml) |
|---|---|---|---|---|
| Ex. 1 | 53 | 11 | 14 | 17.6 |
| Ex. 2 | 50 | 12 | 17 | 28.1 |
| Ex. 3 | 53 | 11 | 13 | 27.4 |
| Com. Ex. 1 | 50 | 11 | 14 | 30.4 |
| Com. Ex. 2 | 52 | 13 | 16 | 31.6 |
| Com. Ex. 3 | 51 | 12 | 12 | 30.4 |

As is obvious from Table 2, the disposable body warmer of the present invention sharply rises and the duration thereof can be made long. Further the generated amount of gas is small and its temperature condition is scarcely varied with time.

What is claimed is:

1. A disposable body warmer comprising a flat inner bag, a heat-generating component which generates heat under presence of air being enclosed in the flat inner bag and an airtight bag enclosing the flat inner bag therein, the heat-generating agent component containing an unheated mixture of potassium chloride, water, water-holding material, activated carbon, iron powder and at least one material selected from sodium thiosulfate and potassium thiosulfate.

2. The disposable body warmer of claim 1, wherein the proportion of the potassium chloride in the heat-generating component is 0.5% to 10%.

3. The disposable body warmer of claim 1, wherein the proportion of the potassium chloride in the heat-generating component is 1.5% to 5.0%.

4. The disposable body warmer of any one of claims 1, 2 and 3, wherein the proportion of the water in the heat-generating component is 10% to 35%.

5. The disposable body warmer of any one of claims 1, 2 and 3, wherein a first self-adhesive layer is formed at least partially on one surface of the flat inner bag.

6. The disposable body warmer of claim 5, wherein the self-adhesive layer is formed in stripe.

7. The disposable body warmer of claim 5, wherein a release layer corresponding to the self-adhesive layer formed on the flat inner bag is formed on an inner surface of the airtight bag.

8. The disposable body warmer of claim 5, wherein a release paper is arranged on the self-adhesive layer, the release paper being provided with at least one slit so that the release paper is partially released.

9. The disposable body warmer of claim 5, further including at least one release paper having on one surface thereof a self-adhesive layer, the release paper being in contact with the first self-adhesive layer such that the self-adhesive layer of the release paper faces in an opposite direction from the flat inner bag.

10. The disposable body warmer of claim 5, wherein the first self-adhesive layer is formed at two locations on one surface of the inner bag and the flat inner bag is folded so that the self-adhesive layer at two locations detachably adheres to itself.

11. The disposable body warmer of claim 5, wherein a release layer is formed on the one surface of the flat inner bag so as to cover the self-adhesive layer when the flat inner bag is folded.

12. The disposable body warmer of claim 1 further including a self-adhesive tongue piece, wherein the tongue piece is provided at one surface thereof with a self-adhesive layer and at one end thereof with a retractable tape, the self-adhesive layer of the tongue piece being fixed on a release layer formed on one surface of the flat inner bag and the tongue piece being fixed to the flat inner bag at one end adjacent the retractable tape.

13. The disposable body warmer of claim 1, wherein the proportion of the water in the heat-generating component is 25% to 30%.

14. The disposable body warmer of claim 1, wherein a self-adhesive tongue piece, being provided at one surface thereof with a self-adhesive layer and a release layer so that they adhere to each other when the tongue piece is folded, is fixed to the flat inner bag at other surface opposite to the one surface where the release layer is formed.

* * * * *